(12) United States Patent
Sekimizu (10) Patent No.: US 10,265,352 B2
(45) Date of Patent: Apr. 23, 2019

(54) LACTIC ACID BACTERIA, NATURAL IMMUNOACTIVATOR AND INFECTION PREVENTATIVE/THERAPEUTIC DERIVED FROM SAID LACTIC ACID BACTERIA, AND FOOD/BEVERAGE

(71) Applicants: GENOME PHARMACEUTICALS INSTITUTE CO., LTD., Tokyo (JP); ANTENNA CO., LTD., Fukuoka-shi, Fukuoka (JP); THE UNIVERSITY OF TOKYO, Tokyo (JP)

(72) Inventor: Kazuhisa Sekimizu, Tokyo (JP)

(73) Assignees: GENOME PHARMACEUTICALS INSTITUTE CO., LTD., Tokyo (JP); ANTENNA CO., LTD., Fukuoka (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/547,865

(22) PCT Filed: Feb. 4, 2016

(86) PCT No.: PCT/JP2016/053378
§ 371 (c)(1),
(2) Date: Aug. 1, 2017

(87) PCT Pub. No.: WO2016/125861
PCT Pub. Date: Aug. 11, 2016

(65) Prior Publication Data
US 2018/0243352 A1 Aug. 30, 2018

(30) Foreign Application Priority Data
Feb. 6, 2015 (JP) .................................. 2015-022567

(51) Int. Cl.
| | |
|---|---|
| A01N 63/00 | (2006.01) |
| A61K 35/747 | (2015.01) |
| A61K 38/00 | (2006.01) |
| A61K 35/74 | (2015.01) |
| C12N 1/20 | (2006.01) |
| A23L 5/00 | (2016.01) |
| A23L 33/10 | (2016.01) |
| A23L 33/135 | (2016.01) |
| A61P 37/04 | (2006.01) |
| A61P 31/04 | (2006.01) |

(52) U.S. Cl.
CPC .............. *A61K 35/747* (2013.01); *A23L 5/00* (2016.08); *A23L 33/10* (2016.08); *A23L 33/135* (2016.08); *A61K 35/74* (2013.01); *A61K 38/00* (2013.01); *A61P 31/04* (2018.01); *A61P 37/04* (2018.01); *C12N 1/20* (2013.01); *A23V 2002/00* (2013.01); *A23Y 2220/00* (2013.01)

(58) Field of Classification Search
CPC ..................................................... A61K 35/747
See application file for complete search history.

(56) References Cited

U.S. PATENT DOCUMENTS

| 2010/0111870 A1 | 5/2010 | Sekimizu et al. |
| 2012/0196352 A1 | 8/2012 | Kim et al. |
| 2013/0064928 A1 | 3/2013 | Iino et al. |

FOREIGN PATENT DOCUMENTS

| EP | 2722386 A1 | 4/2014 |
| JP | 2007-327964 A | 12/2007 |
| JP | 2009-112232 A | 5/2009 |
| JP | 2012-6917 A | 1/2012 |
| WO | 2008/126905 A1 | 10/2008 |
| WO | 2011/010770 A1 | 1/2011 |
| WO | 2011/115114 A1 | 9/2011 |
| WO | 2012/063345 A1 | 5/2012 |
| WO | 2012/108347 A1 | 8/2012 |

OTHER PUBLICATIONS

Kleerebezem et al., "Complete genome sequence of Lactobacillus plantarum WCFS1," Proceedings of the National Academy of Sciences of the United States of America, Feb. 18, 2003, vol. 100, No. 4, pp. 1990-1995, cited in the specification.

Siezen et al., "Complete Resequencing and Reannotation of the Lactobacillus plantarum WCFS1 Genome," Journal of Bacteriology, Jan. 2012, pp. 195-196, cited in the specification.

(Continued)

*Primary Examiner* — Albert M Navarro
(74) *Attorney, Agent, or Firm* — Westerman, Hattori, Daniels & Adrian, LLP (57) ABSTRACT

Lactic acid bacteria having high natural immunity activation ability and infection preventative/therapeutic containing said lactic acid bacteria or elements derived from said lactic acid bacteria, and a food/beverage containing these are provided. Lactic acid bacteria belonging to the genus *Lactobacillus* that are accession number NITE BP-02005 of the NITE NPMD, lactic acid bacteria having natural immunity activation ability that are these lactic acid bacteria or naturally or artificially mutated lactic acid bacteria thereof, lactic acid bacteria having a base sequence of the 16S rDNA region shown by SEQ ID NO: 1, a natural immunity-activating agent having as an active ingredient these lactic acid bacteria, dead cells of these lactic acid bacteria, or a treatment product of these lactic acid bacteria, an infection preventative/therapeutic containing as an active ingredient a peptide glycan of these lactic acid bacteria, and a food/beverage containing these are disclosed.

8 Claims, 3 Drawing Sheets
Specification includes a Sequence Listing.

(56) References Cited

OTHER PUBLICATIONS

Grangette et al., "Mucosal Immune Responses and Protection against Tetanus Toxin after Intranasal Immunization with Recombinant Lactobacillus plantarum," Infection and Immunity, Mar. 2001, vol. 69, No. 3, pp. 1547-1553, cited in the specification.
Seegers, "Lactobacilli as live vaccine delivery vectors: progress and prospects," TRENDS in Biotechnology, vol. 20, No. 12, Dec. 2002, pp. 508-515, cited in the specification.
Ishii et al., "Activation of the Silkworm Cytokine by Bacterial and Fungal Cell Wall Components via a Reactive Oxygen Species-triggered Mechanism," The Journal of Biological Chemistry, vol. 283, No. 4, pp. 2185-2191, Jan. 25, 2008, cited in the specification.
Curk et al., "*Lactobacillus paraplantarum* sp. nov., a New Species Related to Lactobacillus plantarum," International Journal of Systematic Bacteriology, Apr. 1996, vol. 46, No. 2, pp. 595-598, cited in the specification.
Nishida, "Prevention of infection with lactic acid bacteria activating innate immunity," Dai 62 Kai Higashinihon Branch of Japanese Association for Infectious Diseases Gakujutsu Shukai, Dai 60 Kai Higashinihon Branch of Japan Society of Chemotherapy Sokai Godo Gakkai Program Shorokushu, Oct. 7, 2013, p. 76, S8-4, cited in ISR (3 pages, including English translation).
International Search Report dated May 10, 2016, issued in counterpart International Application No. PCT/JP2016/053378 (2 pages).
Extended (supplementary) European Search Report dated Jun. 1, 2018, issued in counterpart European Application No. 16746692.9. (10 pages).

FIG. 1

Lactobacillus paraplantarum strain DSM 10667 16S ribosomal RNA gene, partial sequence
Sequence ID: ref|NR_025447.1| Length: 1502 Number of Matches: 1
Range 1: 31 to 1497

| Score | Expect | Identities | Gaps | Strand | Frame |
|---|---|---|---|---|---|
| 2590 bits(1402) | 0.0() | 1452/1475(98%) | 9/1475(0%) | Plus/Plus | |

Features:

```
Query    7    TGCAAGTCGAACGAACTCTGGTTAATGATTGAAGGTGCTTGCACCTGATTGATTTAACAT    66
              ||||||||||||||||||||||||  |||||||   |||||||||   ||| ||| ||||
Sbjct    31   TGCAAGTCGAACGAACTCTGGT-AATGATT---GGTGCTTGCA--TCA-TGAATT-ACAT   82

Query    67   TTGAGTGAGTGGCGAACTGGTGAGTAACACGTGGGAAACCTGCCCAGAAGTGGGGGATAA   126
              ||||||||||||||||||||||||||||||||||||||||||||||||||  ||||||||
Sbjct    83   TTGAGTGAGTGGCGAACTGGTGAGTAACACGTGGGAAACCTGCCCAGAAGCGGGGGATAA   142

Query    127  CACCTGGAAACAGATGCTAATACCGCATAACAACTCGACCGCATGGTCTGAGTTTAAAA   186
              ||||||||||||||| ||||||||||||||||| ||||||||||||| ||||| ||||
Sbjct    143  CACCTGGAAACAGATCCTAATACCGCATAACAACTTGACCGCATGGTCCGAGTTTGAAA   202

Query    187  GATGGCTTCGGCTATCACTTTTGGATGGTCCCGCGGCGTATTAGCTAGATGGTGAGGTAA   246
              ||||||||||||||||||||||||||||||||||||||||||||||||||||||||||||
Sbjct    203  GATGGCTTCGGCTATCACTTTTGGATGGTCCCGCGGCGTATTAGCTAGATGGTGAGGTAA   262

Query    247  CGGCTCACCATGGCAATGATACGTAGCCCGACCTGAGAGGGTAATCGGCCACATTGGGACT   306
              |||||||||||||||||||||||||||| |||||||||||||||||||||||||||||||
Sbjct    263  CGGCTCACCATGGCAATGATACGTAGCCGACCTGAGAGGGTAATCGGCCACATTGGGACT   322

Query    307  GAGACACGGCCCAAACTCCTACGGGAGGCAGCAGTAGGGAATCTTCCACAATGGACGAAA   366
              ||||||||||||||||||||||||||||||||||||||||||||||||||||||||||||
Sbjct    323  GAGACACGGCCCAAACTCCTACGGGAGGCAGCAGTAGGGAATCTTCCACAATGGACGAAA   382

Query    367  GTCTGATGGAGCAACGCCGCGTGAGTGAAGAAGGGTTTCGGCTCGTAAAACTCTGTTGTT   426
              ||||||||||||||||||||||||||||||||||||||||||||||||||||||||||||
Sbjct    383  GTCTGATGGAGCAACGCCGCGTGAGTGAAGAAGGGTTTCGGCTCGTAAAACTCTGTTGTT   442

Query    427  AAAGAAGAACATATCTGAGAGTAACTGTTCAGGTATTGACGGTATTTAACCAGAAAGCCA   486
              ||||||||||||||||||||||||||||||||||||||||||||||||||||||||||||
Sbjct    443  AAAGAAGAACATATCTGAGAGTAACTGTTCAGGTATTGACGGTATTTAACCAGAAAGCCA   502

Query    487  CGGCTAACTACGTGCCAGCAGCCGCGGTAATACGTAGGTGGCAAGCGTTATCCGGATTTA   546
              ||||||||||||||||||||||||||||||||||||||||||||||||| |||||||||
Sbjct    503  CGGCTAACTACGTGCCAGCAGCCGCGGTAATACGTAGGTGGCAAGCGTTGTCCGGATTTA   562

Query    547  TTGGGCGTAAAGCGAGCGCAGGCGGTTTTTTAAGTCTGATGTGAAAGCCTTCGGCTCAAC   606
              ||||||||||||||||||||||||||||||||||||||||||||||||||||||||||||
Sbjct    563  TTGGGCGTAAAGCGAGCGCAGGCGGTTTTTTAAGTCTGATGTGAAAGCCTTCGGCTCAAC   622

Query    607  CGAAGAAGTGCATCGGAAACTGGGAAACTTGAGTGCAGAAAAGGACAGTGGAACTCCATG   666
              ||||||| |||||||||||||||||||||||||||||||| ||||||||||||||||||
Sbjct    623  CGAAGAAGTGCATCGGAAACTGGGAAACTTGAGTGCAGAAGAGGACAGTGGAACTCCATG   682

Query    667  TGTAGCGGTGAAATGCGTAGATATATGGAAGAACACCAGTGGCGAAGGCGGCTGTCTGGT   726
              ||||||||||||||||||||||||||||||||||||||||||||||||||||||||||||
Sbjct    683  TGTAGCGGTGAAATGCGTAGATATATGGAAGAACACCAGTGGCGAAGGCGGCTGTCTGGT   742

Query    727  CTGTAACTGACGCTGAGGCTCGAAAGTATGGGTAGCAAACAGGATTAGATACCCTGGTAG   786
              ||||||||||||||||||||||||||||||||||||||||||||||||||||||||||||
Sbjct    743  CTGTAACTGACGCTGAGGCTCGAAAGTATGGGTAGCAAACAGGATTAGATACCCTGGTAG   802

Query    787  TCCATACCGTAAACGATGAATGCTAAGTGTTGGAGGGTTTCCGCCCTTCAGTGCTGCAGC   846
              ||||||||||||||||||||| ||||||||||||||||||||||||||||||||||||||
Sbjct    803  TCCATACCGTAAACGATGAATCCTAAGTGTTGGAGGGTTTCCGCCCTTCAGTGCTGCAGC   862

Query    847  TAACGCATTAAGCATTCCGCCTGGGGAGTACGGCCGCAAGGCTAAAACTCAAAGGAATTG   906
              ||||||||||||||||||||||||||||||||||||||||||||| ||||||||||||||
Sbjct    863  TAACGCATTAAGCATTCCGCCTGGGGAGTACGGCCGCAAGGCTGAAACTCAAAGGAATTG   922

Query    907  ACGGGGGCCCGCACAAGCGGTGGAGCATGTGGTTTAATTCGAAGCTACGCGAAGAACCTT   966
              ||||||||||||||||||||||||||||||||||||||||||||||||||||||||||||
Sbjct    923  ACGGGGGCCCGCACAAGCGGTGGAGCATGTGGTTTAATTCGAAGCTACGCGAAGAACCTT   982

Query    967  ACCAGGTCTTGACATACTATGCAAATCTAAGAGATTAGACGTTCCCTTCGGGGACATGGA   1026
              ||||||||||||||||||||||||||||||||||||||||||||||||||||||||||||
Sbjct    983  ACCAGGTCTTGACATACTATGCAAATCTAAGAGATTAGACGTTCCCTTCGGGGACATGGA   1042

Query    1027 TACAGGTGGTGCATGGTTGTCGTCAGCTCGTGTCGTGAGATGTTGGGTTAAGTCCCGCAA   1086
              ||||||||||||||||||||||||||||||||||||||||||||||||||||||||||||
Sbjct    1043 TACAGGTGGTGCATGGTTGTCGTCAGCTCGTGTCGTGAGATGTTGGGTTAAGTCCCGCAA   1102

Query    1087 CGAGCGCAACCCTTATTATTAGTTGCCAGCATTAAGTTGGGCACTCTAGTGAGACTGCCG                1146
```

FIG. 2

```
Sbjct  1103  CGAGCGCAACCCTTATTATCAGTTGCCAGCATTAAGTTGGGCACTCTGGTGACACTGCCG  1162
Query  1147  GTGACAAACCGGAGGAAGGTGGGGATGACGTCAAATCATCATGCCCCTTATGACCTGGGC  1206
Sbjct  1163  GTGACAAACCGGAGGAAGGTGGGGATGACGTCAAATCATCATGCCCCTTATGACCTGGGC  1222
Query  1207  TACACACGTGCTACAATGGATGGTACAACGAGTTGCGAACTCGCGAGAGTAAGCTAATCT  1266
Sbjct  1223  TACACACGTGCTACAATGGATGGTACAACGAGTTGCGAACTCGCGAGAGTAAGCTAATCT  1282
Query  1267  CTTAAAGCCATTCTCAGTTCGGATTGTAGGCTGCAACTCGCCTACATGAAGTCGGAATCG  1326
Sbjct  1283  CTTAAAGCCATTCTCAGTTCGGATTGTAGGCTGCAACTCGCCTACATGAAGTCGGAATCG  1342
Query  1327  CTAGTAATCGCGGATCAGCATGCCGCGGTGAATACGTTCCCGGGCCTTGTACACACCGCC  1386
Sbjct  1343  CTAGTAATCGCGGATCAGCATGCCGCGGTGAATACGTTCCCGGGCCTTGTACACACCGCC  1402
Query  1387  CGTCACACCATGAGAGTTTGTAACACCCAAAGTCGGTGGGGTAACCTTCGGGG-ACCAGC  1445
Sbjct  1403  CGTCACACCATGAGAGTTTGTAACACCCAAAGTCGGTGGGGTAACCTTTTAGGAACCAGC  1462
Query  1446  CGCCTAAGGTGGGACAGATGATTAGGGNGAAGTCG  1480
Sbjct  1463  CGCCTAAGGTGGGACAGATGATTAGGGTGAAGTCG  1497
```

FIG. 3

—◇— Normal diet + non-infection with P. aeruginosa (not injected)
—✶— Normal diet with peptidoglycan of L. plantarum PGN + non-infection with P. aeruginosa (not injected)
—○— Normal diet + P. aeruginosa infection (injected)
—●— Normal diet with peptidoglycan of L. plantarum PGN + P. aeruginosa infection (injected)

LACTIC ACID BACTERIA, NATURAL IMMUNOACTIVATOR AND INFECTION PREVENTATIVE/THERAPEUTIC DERIVED FROM SAID LACTIC ACID BACTERIA, AND FOOD/BEVERAGE

TECHNICAL FIELD

The present invention relates to a novel lactic acid bacterium, an innate immunity activator comprising a viable bacterium, dead bacterium or processed material of the novel lactic acid bacterium as an active ingredient, an agent for preventing or treating infection comprising peptidoglycan of the novel lactic acid bacterium as an active ingredient, and food and drink comprising them.

BACKGROUND ART

Lactic acid bacteria have been traditionally used in fermented food, also used in the manufacture of food and drink, medicines, probiotics and the like. Lactic acid bacteria have characteristics such as gram-positive, catalase-negative, not forming spore, immotile, and the like.

Lactobacillus paraplantarum (L. paraplantarum) is closely related to Lactobacillus plantarum (L. plantarum), and it has been known that L. paraplantarum and L. plantarum are non-pathogenic gram-positive lactic acid bacteria and are heterofermentative (Non-Patent Document 6).

Further, the entire genomes of some species and subspecies of lactic acid bacteria have been sequenced (Non-Patent Documents 1 and 2), and recombinant L. plantarum has been utilized for presenting a specific antigen through the epidermis of intestines and has been recently noted as a viable agent for preventing infection for oral administration (Non-Patent Documents 3 and 4).

On the other hand, it has been known that in a mechanism of innate immunity, immune cells such as macrophages and dendritic cells are responsive to substances activating innate immunity derived from bacteria or viruses to produce cytokines, thereby stimulating subsequent immune reaction. The mechanism of innate immunity is a mechanism for controlling infection that organisms have in common, is generally non-specific, has a good response, and effectively functions against many infectious sources.

In the past, the inventor has developed an evaluation method (a screening method) capable of easily measuring an activity for activating innate immunity, using silkworms having only a mechanism of innate immunity (Patent Document 1 and Non-Patent Document 5). In addition, the inventor has demonstrated that the evaluation method can evaluate or screen an innate immunity activator having activity for activating innate immunity against vertebrates such as humans (Patent Document 1, etc.).

Further, it has been demonstrated by the inventors that silkworms are useful as model animals of evaluating tolerance to infection caused by bacteria (Patent Documents 2, 3, etc.).

Abnormality of an immune mechanism causes various diseases. Thus, the development of an excellent innate immunity activator or agent for preventing or treating infection capable of adjusting such an immune mechanism has been desired. Further, the development of food and drink comprising material derived from lactic acid bacteria or the above agent, and food and drink utilizing the lactic acid bacteria having excellent characteristics has also been desired.

PRIOR ART REFERENCES

Patent Documents

Patent Document 1: WO 2008/126905
Patent Document 2: Japanese Patent Laid-Open Publication No. 2007-327964
Patent Document 3: Japanese Patent Laid-Open Publication No. 2012-006917

Non Patent Documents

Non-Patent Document 1: Kleerebezem M, Boekhorst J, van Kranenburg R, Molenaar D, Kuipers O P, Leer R, Tarchini R, Peters S A, Sandbrink H M, Fiers M W, Stiekema W, Lankhorst R M, Bron P A, Hoffer S M, Groot M N, Kerkhoven R, de Vries M, Ursing B, de Vos W M, Siezen R J. Complete genome sequence of Lactobacillus plantarum WCFS1. Proc Natl Acad Sci USA. 2003 Feb. 18; 100(4):1990-5

Non-Patent Document 2: Siezen R J, Francke C, Renckens B, Boekhorst J, Wels M, Kleerebezem M, van Hijum S A. Complete resequencing and reannotation of the Lactobacillus plantarum WCFS1 genome. J Bacteriol. 2012 January; 194(1):195-6.

Non-Patent Document 3: Grangette C, Muller-Alouf H, Goudercourt D, Geoffroy M C, Turneer M, Mercenier A. Mucosal immune responses and protection against tetanus toxin after intranasal immunization with recombinant Lactobacillus plantarum. Infect Immun. 2001 March; 69(3):1547-53.

Non-Patent Document 4: Seegers J F. Lactobacilli as live vaccine delivery vectors: progress and prospects. Trends Biotechnol. 2002 December; 20(12):508-15.

Non-Patent Document 5: Ishii K, Hamamoto H, Kamimura M, Sekimizu K. Activation of the silkworm cytokine by bacterial and fungal cell wall components via a reactive oxygen species-triggered mechanism. J Biol Chem. 2008 Jan. 25; 283(4):2185-91.

Non-Patent Document 6: Curk M C, Hubert J C, Bringel F. Lactobacillus paraplantarum sp. now, a new species related to Lactobacillus plantarum. Int J Syst Bacteriol. 1996 April; 46(2):595-8.

SUMMARY OF THE INVENTION

Problems to be Solved by the Invention

An object of the present invention is to provide a novel lactic acid bacterium having a high activity for activating innate immunity, an innate immunity activator comprising the lactic acid bacterium or dead bacterium or processed material of the lactic acid bacterium as an active ingredient, and food and drink comprising the lactic acid bacterium or an innate immunity activator derived from the lactic acid bacterium.

Further, the object thereof is to provide an agent for preventing or treating infection or food and drink comprising material derived from novel lactic acid bacterium as an active ingredient.

Means for Solving the Problems

The present inventor have earnestly investigated to solve the above problems, and as a result, the inventor has found that a specific lactic acid bacterium has an higher activity for activating innate immunity than that of ones which have been known to have an activity for activating innate immunity and that of other lactic acid bacterium such as a lactic acid bacterium belonging to genus *Lactobacillus*.

Further, the inventor has found that the lactic acid bacterium having an activity for activating innate immunity is a novel lactic acid bacterium belonging to genus *Lactobacillus* (hereinafter sometimes abbreviated as "#11-1"), from the results of analysis of properties thereof, analysis of the nucleotide sequence of 16S rDNA thereof and the like.

Further, the inventor has unexpectedly found that silkworms eating peptidoglycan fraction of the lactic acid bacterium has longer survival time after infection with *Pseudomonas aeruginosa* and has tolerance to the infection with *Pseudomonas aeruginosa*, even though the silkworms do not have a mechanism of acquired immunity, whereby they have accomplished the present invention.

That is, the present invention is directed to a lactic acid bacterium belonging to genus *Lactobacillus* with Accession No. NITE BP-02005 in NITE Patent Microorganisms Depositary (NPMD) of Incorporated Administrative Agency National Institute of Technology and Evaluation (NITE).

The present invention is further directed to a lactic acid bacterium isolated or purified from the lactic acid bacterium.

The present invention is also directed to the above lactic acid bacterium or naturally or artificially mutated lactic acid bacterium thereof, wherein the lactic acid bacterium has an activity for activating innate immunity.

The present invention is also directed to the above lactic acid bacterium, wherein the lactic acid bacterium has the nucleotide sequence of the 16S rDNA region shown in SEQ ID No: 1.

The present invention is further directed to a lactic acid bacterium isolated or purified from the lactic acid bacterium.

The present invention is also directed to an innate immunity activator comprising the above lactic acid bacterium of the present invention, a dead bacterium of the lactic acid bacterium or a processed material of the lactic acid bacterium as an active ingredient, wherein the processed material of the lactic acid bacterium is at least one of the processed materials selected from the group consisting of cultured material, concentrated material, paste material, dried material, fluid material, diluted material, crushed material, sterilized material of the lactic acid bacteria, and extract from the cultured material.

The present invention is also directed to an agent for preventing or treating infection comprising peptidoglycan of the above lactic acid bacterium as an active ingredient.

The present invention is also directed to an agent for preventing or treating infection comprising the above innate immunity activator as an active ingredient.

The present invention is also directed to an agent for preventing or treating infection comprising peptidoglycan of the above lactic acid bacterium as an active ingredient.

The present invention is also directed to food and drink comprising the above lactic acid bacterium, innate immunity activator or agent for preventing or treating infection.

The present invention is also directed to food and drink manufactured by a fermentation process using the above lactic acid bacterium, and the food and drink being fermented milk.

Effects of the Invention

According to the present invention, a novel lactic acid bacterium having a significantly high activity for activating innate immunity can be provided.

Further, the present invention can provide a novel innate immunity activator having a significantly high activity for activating innate immunity which comprises the novel lactic acid bacterium, a dead bacterium of the lactic acid bacterium or a processed material of the lactic acid bacterium as an active ingredient, and food and drink having an excellent activity for activating innate immunity which comprises or is derived from the lactic acid bacterium or the innate immunity activator.

In addition, according to the present invention, an agent for preventing or treating infection comprising peptidoglycan of the novel lactic acid bacterium as an active ingredient can be provided, and oral administration of the agent for preventing or treating infection can prevent infection caused by bacteria and the like. Thus, food and drink comprising the agent for preventing or treating infection is effective for infection.

In a screening method having found a novel lactic acid bacterium or a novel innate immunity activator of the present invention, silkworm muscle contraction with response to substances activating innate immunity is utilized, the detection of a false-positive activity for activating innate immunity with LPS is suppressed, and with measurements using silkworm, measurement result taking ADME (absorption, distribution, metabolism, and excretion) or PK (pharmacokinetics) of the samples into consideration can be obtained and compounds having toxicity can be removed.

Thus, the innate immunity activator, agent for preventing or treating infection and food and drink of the present invention has excellent effect since they have passed the above test.

The lactic acid bacterium of the present invention can be utilized not only to manufacture common food and drink, health food, medicine, fermented food and drink, probiotics and the like, but also to prevent or treat disease with innate immune activation. As fermented food and drink, it is more preferably that the lactic acid bacterium is used in fermented milk, lactic acid bacteria beverage, yogurt, pickles, and a starter for manufacturing pickles. Further, the lactic acid bacterium not sensitive to acid can be delivered to small intestine without being decomposed in stomach.

BRIEF DESCRIPTION OF DRAWINGS

FIG. 1 a chart showing the result of homology analysis of 16S rDNA of *Lactobacillus paraplantarum* #11-1 of the present invention and 16S rDNA of *Lactobacillus paraplantarum* DSM10667 (NR-025447.1) being closely related thereto, using BLAST.

EMBODIMENTS TO CARRY OUT THE INVENTION

Hereinafter, the present invention will be described, but the present invention is not limited by the following specific embodiments, and can be practiced by optionally modifying these.

<Lactic Acid Bacterium>

The present invention is a lactic acid bacterium belonging to genus *Lactobacillus* with Accession No. NITE BP-02005 in NITE Patent Microorganisms Depositary (NPMD) of Incorporated Administrative Agency National Institute of Technology and Evaluation (NITE).

The detailed description of the novel lactic acid bacterium (#11-1) belonging to genus *Lactobacillus* is as follows.

Morphology: #11-1 of the present invention was isolated from rice bran pickles, for the first time.

Growth Situation in Culture Medium:
(1) On GAM medium and MRS agar medium, white colony is formed. Diffusing color pigments are not found.
(2) On MRS agar medium with calcium carbonate, zone of transparency with production of lactic acid is formed.

Physiological Properties:
Physiological and chemical classification properties of #11-1 of the present invention are as follows.
(1) Behavior to oxygen: aerobiotic
(2) Catalase: −
(3) Alkaline phosphatase: −
(4) Esterase: −
(5) Esterase lipase: −
(6) Lipase: −
(7) Leucine arylamidase: +
(8) Valine arylamidase: +
(9) Cysteine arylamidase: −
(10) Trypsin: −
(11) α-Chymotrypsin: −
(12) Acid phosphatase: +
(13) Naphthol-AS-BI-phosphohydrolase: +
(14) α-Galactosidase: −
(15) β-Galactosidase: −
(16) β-Glucuronidase: −
(17) α-Glucosidase: −
(18) β-Glucosidase: −
(19) N-Acetyl-β-glucosaminidase: −
(20) α-Mannosidase: −
(21) α-Fucosidase: −
(22) Production ability of acid and gas from the following sugars and the like:
Glycerol: −
Erythritol: −
D-Arabinose: −
L-Arabinose: −
D-Ribose: ±
D-Xylose: −
L-Xylose: −
D-Adonitol: −
Methyl-β-D-xylopyranoside: −
D-Galactose: +
D-Glucose: +
D-Fructose: +
D-Mannose: +
L-Sorbose: −
L-Rhamnose: −
Dulcitol: −
Inositol: −
D-Mannitol: +
D-Sorbitol: −
Methyl-α-D-mannopyranoside: −
Methyl-α-D-glucopyranoside: +
N-Acetyl glucosamine: +
Amygdalin: ±
Arbutin: +
Esculin: +
Salicin: +
D-Cellobiose: +
D-Maltose: +
D-Lactose: −
D-Melibiose: −
D-Sucrose: +
D-Trehalose: +
Insulin: −
D-Melezitose: −
D-Raffinose: −
Starch: −
Glycogen: −
Xylitol: −
Gentiobiose: +
D-Turanose: −
D-Lyxose: −
D-Tagatose: −
D-Fucose: −
L-Fucose: −
D-Arabitol: −
L-Arabitol: −
Gluconate: ±
2-Keto-gluconate: −
5-Keto-gluconate: −

Molecular Biological Analysis Results:
Analysis results of #11-1 with regard to 16S rDNA in accordance with guidance of the molecular biological systematic classification are as follows.

Nucleotide sequence of the 16S rDNA region from genome DNA of #11-1 was amplified by PCR and it was analyzed by a sequencer; and as a result, nucleotide sequence of almost entire length of the 16S rDNA was obtained.

When homology search of this nucleotide sequence was performed using BLAST analysis of NCBI, the nucleotide sequence of the 16S rDNA region of #11-1 showed 98% homology relative to the nucleotide sequence of *Lactobacillus paraplantarum* DSM10667 strain (Accession No. NR_025447.1), and #11-1 belongs to *L. plantarum paraplantarum*.

However, the nucleotide sequence of the 16S rDNA region of #11-1 do not completely correspond to that of *Lactobacillus paraplantarum* DSM10667 strain, #11-1 of the present invention is a lactic acid bacterium strain (subspecies) different from the above strain.

By referring the physiological and chemical classification properties of #11-1 as described above to classification according to Bergey's Manual of Systematic Bacteriology, vol. 3 1989 and to description in other references, together with analysis results of 16S rDNA, #11-1 of the present invention is a novel microorganism belonging to genus *Lactobacillus*.

Comparing with the known strains belonging to genus *Lactobacillus*, #11-1 has the highest activity for activating innate immunity, and #11-1 was comprehensively determined to be a novel isolated microorganism strain.

190 11-1 was domestically deposited on Feb. 5, 2015 to NITE Patent Microorganisms Depositary (NPMD) of Incorporated Administrative Agency National Institute of Technology and Evaluation (hereinafter abbreviated as "NITE"), the address of which is Room 122, 2-5-8 Kazusakamatari, Kisarazu-shi, Chiba, with Accession No. NITE P-02005.

11-1 was then transferred to the international deposition (transfer date (international deposition date): Jan. 28, 2016) from the domestic deposition (original deposition date: Feb. 5, 2015) by requesting to convert the original deposit to a deposit under the Budapest Treaty to NITE Patent Microorganisms Depositary (NPMD) of Incorporated Administrative Agency National Institute of Technology and Evaluation (NITE), the address of which is Room 122, 2-5-8 Kazusakamatari, Kisarazu-shi, Chiba; as a result of viability statement and acceptance of the transfer request, Accession No. "NITE BP-02005" was given.

As the general properties of a bacterium, properties of the strain thereof tend to be mutated easily; and thus, there is a possibility that the physiological properties of #11-1 do not stay as they are shown above. Further, needless to say, "mutation" described above includes both natural mutation and artificial mutation.

A method for culturing #11-1 is as follows. The method for culturing #11-1 may be one in accordance with a general method for culturing genus *Lactobacillus*.

It is preferable that the culture is under an anaerobic condition. As to the carbon source in the culture medium, organic carbon compounds such as D-ribose, D-galactose, D-glucose, D-fructose, D-mannose, D-mannitol, N-acetylglucosamine, amygdalin, arbutin, esculin, salicin, D-cellobiose, D-maltose, sucrose, D-trehalose, gentiobiose, syrup, starch syrup, fats and oils may be used, and as to the nitrogen source, organic or inorganic nitrogen compounds such as meat extract, casein, peptone, yeast extract, dry yeast, germ, powdered soybean, urea, amino acid, and ammonium salt may be used.

Further, inorganic salts such as sodium salt, potassium salt, calcium salt, magnesium salt, phosphate salt, iron salt, copper salt, zinc salt, and cobalt salt may be added as necessary. Further, addition of a growth accelerator such as biotin, vitamin B1, cysteine, methyl oleate, and lard oil is preferable in order to increase a production amount of the intended substance.

In addition, an antifoaming agent such as a silicone oil and surfactant may be added. As to a culture medium prepared, for example, MRS medium or GAM medium is preferably used.

As described above, the culture condition may be one in accordance with a general method for culturing genus *Lactobacillus*. Static culture is preferable as liquid culture. In a case of culturing the bacterium in a small scale, static culture using a glass bottle with a lid may be used.

It is preferable to keep the culture temperature at 25 to 37° C., more preferably at 32 to 37° C. As to the pH during culture, around 7 is preferable. Culturing period is variable depending on the factor such as the composition of a culture medium used and culture temperature, for example, in a case of #11-1, culturing period is preferably 12 to 72 hours and more preferably 24 to 48 hours, during which time a sufficient amount of the intended substance can be secured.

It is preferable that a colony obtained by culture is picked up to form a single colony on a culture medium again.

<Innate Immunity Activator>

The novel lactic acid bacterium #11-1 according to the present invention is the lactic acid bacterium or naturally or artificially mutated lactic acid bacterium thereof, wherein the lactic acid bacterium has an activity for activating innate immunity.

That is, the present invention is a lactic acid bacterium belonging to genus *Lactobacillus* with Accession No. NITE BP-02005 or naturally or artificially mutated lactic acid bacterium thereof, wherein the lactic acid bacterium has an activity for activating innate immunity.

Measurement of an activity for activating innate immunity was performed using a method described in detail in Example, that is, a method utilizing gradual muscle contraction of silkworms described in detail in Ishii K., Hamamoto H., Kamimura M., Sekimizu K., J. Biol. Chem. January 25; 283(4):2185-91 (2008).

Any of "#11-1, or naturally or artificially mutated lactic acid bacterium thereof", "a dead bacterium of the lactic acid bacterium", and "a processed material of the lactic acid bacterium" has an activity for activating innate immunity.

As to "the processed material of the lactic acid bacterium", the examples are at least one of the processed materials selected from the group consisting of cultured material, concentrated material, paste material, dried material, fluid material, diluted material, crushed material, sterilized material of the lactic acid bacterium, and extract from the cultured material. Examples of "dried material" are spray-dried material, freeze-dried material, vacuum-dried material, drum-dried material.

Another aspect of the present invention is an innate immunity activator comprising "the above lactic acid bacterium of the present invention (#11-1, or naturally or artificially mutated lactic acid bacterium thereof), a dead bacterium of the lactic acid bacterium or a processed material of the lactic acid bacterium as an active ingredient, wherein the processed material of the lactic acid bacterium is at least one of the processed materials selected from the group consisting of cultured material, concentrated material, paste material, dried material, fluid material, diluted material, crushed material, sterilized material of the lactic acid bacteria, and extract from the cultured material.

The innate immunity activator of the present invention can comprise the lactic acid bacterium of the present invention, a dead bacterium of the lactic acid bacteria or processed material of the lactic acid bacteria in various states. The examples of states are a suspension, a lactic acid bacteria cell, a medium supernatant, a medium ingredient, and the like.

As to the lactic acid bacterium, a viable bacterium, a wet bacterium, a dried bacterium and the like can be properly used. Further, the dead bacterium subjected to sterilization such as heat sterilization, sterilization by irradiation, crushing and the like, can be used.

The content of lactic acid bacteria, dead bacteria of the lactic acid bacteria or processed material of the lactic acid bacteria, as an active ingredient, in the innate immunity activator of the present invention is not particularly restricted; and thus, the content thereof can be appropriately selected depending on its purpose. When the whole of innate immunity activator is 100 parts by mass, "the total amount of lactic acid bacteria, dead bacteria of the lactic acid bacteria or processed material of the lactic acid bacteria" is preferably 0.001 to 100 parts by mass, more preferably 0.01 to 99 parts by mass, even more preferably 0.1 to 95 parts by mass, still more preferably 1 to 90 parts by mass.

The active ingredient may be used alone or in combination of two or more. When two or more substances are combined, a content ratio of the respective active ingredients in the innate immunity activator is not particularly limited, and can be appropriately selected depending on the purpose.

The innate immunity activator of the present invention comprising the lactic acid bacteria, dead bacteria of the lactic acid bacteria or processed material of the lactic acid bacteria can also comprise an "other ingredient".

The examples of the "other ingredient" in the innate immunity activator, but are not limited to, can be appropriately selected depending on the purpose, and are a pharmaceutically acceptable carrier and the like.

The carrier is not particularly limited and can be appropriately selected depending on the following dosage form. In addition, the content of "other ingredient" in the innate immunity activator is not particularly limited and can be appropriately selected depending on the purpose.

<Agent for Preventing or Treating Infection>

The lactic acid bacterium of the present invention, dead bacterium of the lactic acid bacterium or processed material of the lactic acid bacterium have an activity for activating innate immunity, is useful as an agent for preventing or treating infection, or an agent for preventing or treating infection for oral administration.

The inventor demonstrated that oral administration of peptidoglycan of lactic acid bacteria of the present invention induced the extended survival of silkworms infected with *P. aeruginosa*. It has been already demonstrated that tolerance of silkworms infected by bacteria is correlated with tolerance of mammals such as humans (For example, Patent Document 2, 3, etc.).

Specifically, it was demonstrated that peptidoglycan of *Lactobacillus plantarum* provided tolerance to *P. aeruginosa* infection to silkworms.

Silkworms have no mechanism of acquired immunity, and cannot produce antibodies against antigens. Thus, it was thought that the orally administered peptidoglycan of *Lactobacillus plantarum* activated a mechanism of innate immunity of intestine and the like of the silkworm, and exhibited effect on infection control.

It has been known that in a case of orally administering peptidoglycan of bacteria to animals, such as mice, having a mechanism of acquired immunity, immunity is given to the animal.

However, the present invention demonstrated that peptidoglycan of lactic acid bacteria provided tolerance to *P. aeruginosa* infection to silkworms having only a mechanism of innate immunity, not having a mechanism of acquired immunity. It was thought that the peptidoglycan activated a mechanism of innate immunity of silkworms and the silkworms had tolerance to infection, and it was suggested that an innate immunity activator comprising lactic acid bacteria of the present invention, dead bacteria of the lactic acid bacteria or processed material of the lactic acid bacteria can be used as an agent for preventing or treating infection for animals such as mammals having the mechanism of innate immunity.

An agent comprising peptidoglycan of lactic acid bacteria belonging to genus *Lactobacillus*, such as *Lactobacillus plantarum*, *Lactobacillus paraplantarum* and the like, as an active ingredient can be used as an agent for preventing or treating infection for mammals such as humans.

Thus, an another aspect of the present invention is an agent for preventing or treating infection comprising the above innate immunity activator as an active ingredient, or an agent for preventing or treating infection comprising peptidoglycan of the above lactic acid bacteria as an active ingredient.

<Medicine; Food and Drink; Health Food and the Like>

Lactic acid bacteria of the present invention or the innate immunity activator of the present invention derived from the lactic acid bacterium can be blended in medicines, quasi-drugs, food and drink having standards such as common food and drink, health food and powdered milk, and can also be used in various medicines and food and drink in any form.

Food and drink, especially fermented milk, manufactured by a fermentation process using the lactic acid bacteria of the present invention is preferable in terms of exhibiting effect of lactic acid bacteria or specific effect of the present invention.

The dosage form of the innate immunity activator or agent for preventing or treating infection of the present invention is not particularly limited, and can be appropriately selected depending on the following desired administration method.

The examples of dosage forms are oral solid agents (tablets, coated tablets, granules, powders, hard capsules, soft capsules and the like), oral liquid agents (liquid agents for internal use, syrup agents, elixir agents and the like), injectable agents (solutions, suspensions and the like), ointments, patches, gel agents, cream agents, powders for external use, spray agents and powders for inhalation.

The oral solid agents can be produced, for example, by adding an excipient to the active ingredient, and further if necessary adding additives such as a binder, a disintegrant, a lubricant, a coloring agent, and a flavoring agent thereto, with a standard method.

The excipient includes, for example, lactose, saccharose, sodium chloride, glucose, starch, calcium carbonate, kaolin, fine crystalline cellulose and silic acid.

The binder includes, for example, water, ethanol, propanol, simple syrup, a glucose solution, a starch solution, a gelatin solution, carboxymethylcellulose, hydroxypropylcellulose, hydroxypropyl starch, methylcellulose, ethylcellulose, shellac, calcium phosphate and polyvinyl pyrrolidone.

The disintegrant includes, for example, dry starch, sodium alginate, agar powder, sodium hydrogen carbonate, calcium carbonate, sodium lauryl sulfate, monoglyceride stearate and lactose.

The lubricant includes, for example, purified talc, stearate salts, borax and polyethylene glycol.

The coloring agent includes, for example, titanium oxide and iron oxide.

The flavoring agent includes, for example, saccharose, orange peel, citric acid and tartaric acid.

The oral liquid agent can be produced, for example, by adding the additives, e.g., the flavoring agent, a buffer and a stabilizer to the active ingredient, with the standard method.

The flavoring agent includes, for example, saccharose, orange peel, citric acid and tartaric acid. The buffer includes, for example, sodium citrate. The stabilizer includes, for example, tragacanth, gum Arabic and gelatin.

The injectable agents for subcutaneous, intramuscular and intravenous injections can be produced with the standard method, for example, by adding a pH adjuster, the buffer, the stabilizer, a tonicity agent and a local anesthetic to the active ingredient.

The pH adjuster and the buffer include, for example, sodium citrate, sodium acetate and sodium phosphate. The stabilizer includes, for example, sodium pyrosulfite, EDTA, thioglycolic acid and thiolactic acid. The tonicity agent includes, for example, sodium chloride and glucose. The local anesthetic includes, for example, procaine hydrochloride and libocaine hydrochloride.

The ointment can be produced by combining a publicly known base, the stabilizer, a wetting agent and a preservative with the active ingredient and mixing them, with the standard method.

The base includes, for example, liquid paraffin, white petrolatum, refined bee wax, octyldodecyl alcohol and paraffin. The preservative includes, for example, methyl paraoxybenzoate, ethyl paraoxybenzoate and propyl paraoxybenzoate.

The patch can be produced by applying the cream agent, the gel agent or the paste agent as the ointment on a publicly known support, with the standard method. The support includes, for example, cottons, staple fibers, wovens and non-wovens composed of chemical fibers, films of soft vinyl chloride, polyethylene and polyurethane, and foam sheets.

The innate immunity activator of the present invention or the agent for preventing or treating infection can be suitably used for individuals who require the activation of a mechanism of innate immunity, individuals who want to acquire acquired immunity against bacteria.

Specifically, for example, the agent can be used by administering it to individuals who require health maintenance and recovery from fatigue, individuals who require the prevention or the treatment of cancers or lifestyle-related diseases, individuals infected with bacteria, fungi or viruses, and the like.

Animals subjected to the administration of the innate immunity activator or agent for preventing or treating infection of the present invention is not particularly limited, can be appropriately selected depending on the purpose, and include, for example, humans; experimental animals such as mice and rats; monkeys; horses; domestic animals such as cattle, swines, goats, chickens; pets such as cats and dogs; and the like.

The method of administering the innate immunity activator is not particularly limited, can be appropriately selected depending on the dosage form of the innate immunity activator, and includes oral administration, intraperitoneal administration, injection into the blood and injection into the intestine. The oral administration is preferable in terms of easily exhibiting the effect.

A dosage of the innate immunity activator or the agent for preventing or treating infection is not particularly limited, can be appropriately selected depending on an age, a body weight and a degree of desired effects in an individual to be administered, and for example, is preferably 1 mg to 30 g, more preferably 10 mg to 10 g and even more preferably 100 mg to 3 g as the active ingredient per day for an adult.

In addition, an administration period of the innate immunity activator or the agent for preventing or treating infection is not particularly limited, can be appropriately selected depending on the purpose, and for example, may be administered preventively or may be administered therapeutically.

The content of the lactic acid bacteria, innate immunity activator or agent for preventing or treating infection, in food and drink comprising the lactic acid bacteria of the present invention, dead bacteria or processed material of the lactic acid bacteria, innate immunity activator or agent for preventing or treating infection (hereinafter sometimes abbreviated as "food and drink of the present invention"), is not particularly limited, can be appropriately selected depending on the purpose and aspect (kind) of drink and food. When the whole of food and drink is 100 parts by mass, the total amount is preferably 0.001 to 100 parts by mass, more preferably 0.01 to 100 parts by mass, even more preferably 0.1 to 100 parts by mass.

In the food and drink, the lactic acid bacteria of the present invention, dead bacteria or processed material of the lactic acid bacteria, innate immunity activator or agent for preventing or treating infection may be used alone or in combination of two or more. When two or more substances are combined, a content ratio of the respective substances in the food and drink is not particularly limited, and can be appropriately selected depending on the purpose.

Food and drink of the present invention has an activity for activating innate immunity and/or an activity for preventing or treating infection.

Food and drink of the present invention comprising the innate immunity activator or agent for preventing or treating infection of the present invention can comprise an "other ingredient".

The "other ingredient" is not particularly limited, can be appropriately selected depending on the purpose within the range in which the effects of the present invention are not impaired, and includes, for example, various food raw materials. In addition, the content of "other ingredient" is not particularly limited and can be appropriately selected depending on the purpose.

Lactic acid bacteria of the present invention can be used for manufacturing common food and drink, health food, medicines, fermented food and drink, probiotics and the like. As to fermented food and drink, the lactic acid bacteria are preferably used in fermented milk, lactic acid beverage, yogurt, pickles, and starters of lactic acid bacteria for manufacturing pickles.

The kinds of the food are not particularly limited, can be appropriately selected depending on the purpose, and include, for example, sweet snacks such as jellies, candies, chocolates, biscuits and gummi candies; taste beverages such as green tea, black tea, coffee and soft drinks; dairy products such as fermented milk, yogurts and ice creams; processed vegetable or fruit products such as vegetable beverages, fruit beverages and jams; liquid foods such as soups; processed grain products such as breads and noodles; various seasonings and the like. Dairy products such as yogurts and fermented milk are preferable.

The method of manufacturing the food is not particularly limited, and can be appropriately manufactured depending on, for example, the food can be manufactured by the method of manufacturing the ordinary various foods.

The food may be manufactured as the oral solid agents, e.g., the tablet, the granule and the capsule, and the oral liquid agents, e.g., the liquid agent for internal use and the syrup agent. The method of manufacturing the oral solid agent and the oral liquid agent is not particularly limited, can be manufactured, for example, according to the method of manufacturing the oral solid agent and the oral liquid agent of the medicines described above.

Food and drink of the present invention is especially useful as functional food, health food and the like for the purpose of activating a mechanism of innate immunity or acquiring tolerance to infection.

In a case where lactic acid bacteria of the present invention, dead bacteria or processed material thereof are used in manufacturing food and drink, the manufacturing method known for a person skilled in the art can be used. The person skilled in the art can manufacture intended food and drink by an appropriate combination of a process of mixing viable or dead lactic acid bacteria or processed material of lactic acid bacteria of the present invention with other ingredients, a forming process, sterilization process, a fermentation process, a heating process, a drying process, a cooling process, a granulation step, packaging step and the like.

Further, when manufacturing various fermented milk using lactic acid bacteria of the present invention, the fermented milk can be manufactured using a method known to a person skilled in the art. The examples include food and drink manufactured by using a process of adding a required amount of lactic acid bacteria of the present invention, as dead bacteria, to fermented milk, and food and drink manufactured by using a process of performing fermentation using lactic acid bacteria of the present invention as starters of lactic acid bacteria.

When performing fermentation using lactic acid bacteria of the present invention as the starters of lactic acid bacteria, the culture conditions can be similar to the culture conditions of the lactic acid bacteria of the present invention.

EXAMPLES

Hereinafter, the present invention will be explained more specifically by showing Examples; but the present invention is not limited to them unless beyond its scope.
<Materials>
<<Medium and Culture Conditions>>

GAM medium and MRS agar medium were respectively purchased from Nissui and BD (Becton Dickinson). Calcium carbonate ($CaCO_3$) was added as necessary.

AnaeroPak (registered trademark) (Mitsubishi gas chemicals) was used for anaerobic culturing.
<<Isolation of Lactic Acid Bacteria>>

Rice bran pickles were used as fermented food. Liquid suspended in saline (0.9 mass % NaCl) was spread on MRS medium, and anaerobically cultured at 37° C. for 2 days.

The colonies were picked up and re-streaked on $CaCO_3$-MRS medium to form a single colony.

The result of measurements of an activity for activating innate immunity using the following method, a lactic acid bacteria strain (#11-1) with an excellent activity for activating innate immunity was obtained. That is, a strain of lactic acid bacteria (#11-1) was isolated.

Lactic acid fermentation was obtained with the formation of white colonies on $CaCO_3$-MRS medium and the formation of transparent band, and it was confirmed that #11-1 was lactic acid bacteria. It is also confirmed that the colonies are gram-stained and #11-1 was gram-positive.
<<Identification of Lactic Acid Bacteria>>

16S rDNA fragments were obtained by colony PCR using PCR enzyme KOD FX Neo (Toyobo), primers 9F and 1541R.

The sequences were determined with Direct sequencing using BigDye (registered trademark) Terminator v3.1 Cycle Sequencing Kit, and ABI PRISM (registered trademark) 3100 Genetic Analyzer.

Information on the sequence was analyzed from 16S ribosomal RNA sequences database (Bacterium and Archaea, 7,545 sequences), using NCBI BLASTN 2.2.27+ (8).

The nucleotide sequence of 16S rDNA region of #11-1 is shown in SEQ ID NO: 1 in the Sequence Listing.

Figure 2:
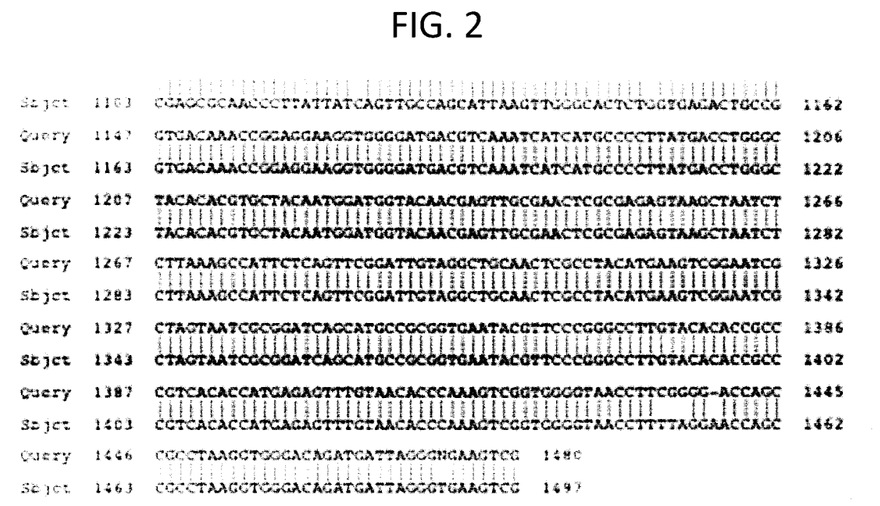
FIG. 2 is a chart continuous to FIG. 1.

The nucleotide sequence of 16S rDNA was determined, homology of the nucleotide sequence was analyzed by BLAST analysis, and the nucleotide sequence had high homology with a lactic acid bacterium as shown in FIGS. 1 and 2.

As shown in FIGS. 1 and 2, this nucleotide sequence was closely related to a *L. paraplantarum* DSM10667 strain (nucleotide sequence: NR_025447.1), but not completely corresponded with each other, and #11-1 was novel "*L. paraplantarum*".
<<Deposit>>

As described above, "#11-1" of the present invention used in Examples was isolated from rice bran pickles, and was domestically deposited on Feb. 5, 2015, as a lactic acid bacterium #11-1 belonging to genus *Lactobacillus*, to NITE Patent Microorganisms Depositary (NPMD) of Incorporated Administrative Agency National Institute of Technology and Evaluation (NITE), authorized as depositary institution under Regulations under the Patent Act and international depositary authority under Budapest Treaty on the international recognition of the deposit of microorganisms for the purpose of patent procedure, the address of which is Room 122, 2-5-8 Kazusakamatari, Kisarazu-shi, Chiba, with Accession No. NITE P-02005.

11-1 was then transferred to the international deposition (transfer date (international deposition date): Jan. 28, 2016) from the domestic deposition (original deposition date: Feb. 5, 2015) by requesting to convert the original deposit to a deposit under the Budapest Treaty to NITE Patent Microorganisms Depositary (NPMD) of Incorporated Administrative Agency National Institute of Technology and Evaluation (NITE), the address of which is Room 122, 2-5-8 Kazusakamatari, Kisarazu-shi, Chiba; as a result of viability statement and acceptance of the transfer request, Accession No. "NITE BP-02005" was given.

Example 1

<Measurement of Activity for Activating Innate Immunity>

The *Lactobacillus paraplantarum* #11-1 (*L. paraplantarum* #11-1) strain cultured on MRS medium overnight was subjected to sterilization at 121° C. for 20 minutes, and 50 μL of the sterilized strain was injected into muscle specimen without head of fifth instar silkworm, and an activity for activating innate immunity was measured with gradual muscle contraction.

Measurement of an activity for activating innate immunity with gradual muscle contraction was conducted in accordance with a method described in Ishii K., Hamamoto H., Kamimura M., Sekimizu K., J. Biol. Chem. January 25; 283(4):2185-91 (2008).

That is, 0.05 mL of samples of which the concentrations of substance to be measured were plural stages were respectively injected into the blood of muscle specimen without head of fifth instar silkworm, and the body length was measured when contracted length was maximum (about ten minutes later).

"C value (Contraction Value)" was obtained by subtracting the body length after injection from the body length before injection, and dividing the subtracted value by the body length before injection, [(the body length before injection)−(the body length after injection)]/(the body length before injection), and C value of 0.15 was defined as 1 U (unit).

C value was measured with dilution obtained by diluting the samples with 0.9% saline to 1-, 4-, 16- 64-, 256-fold respectively, "mass of substance to be measured administered to silkworm" providing 1 U (C value=0.15) was calculated from a graph of which the X-axis indicated the concentration of substance to be measured and the Y-axis indicated C value and units (U) per unit mass were calculated, thereby evaluating an activity for activating innate immunity of substance to be measured.

In addition, 0.05 mL of saline as negative control (tolerance of C value of 0.05 or less), 0.2 mL of air as positive control (tolerance of C value of 0.2 to 0.4) were measured.

Comparative Examples 1 to 3

With the exception of using gram-positive bacteria #4, #11-2 and A shown in Table 1 instead of the *Lactobacillus paraplantarum* #11-1 (*L. paraplantarum* #11-1) strain in Example 1, an activity for activating innate immunity was measured with muscle contraction of silkworms in the same matter as Example 1.

The following Table 1 shows origin and properties of Example 1 and Comparative Examples 1 to 3. As a reference, closely related strain and homology of the strain are shown in Table 1.

The following Table 2 shows the measurement result of an activity for activating innate immunity.

TABLE 1

| No. | Strain | Origin | Gram stain | Reference Upper line: Closely related strain Lower line: Accession Number | homology (%) |
|---|---|---|---|---|---|
| Example 1 | #11-1 | Rice bran pickles | Gram positive Bacilli | *Lactobacillus plantarum* WCFS1 NR_075041.1 | 99 |
| Comparative Example 1 | #4 | Rice bran pickles | Gram positive Bacilli | *Lactobacillus sakei* 23K NR_075042.1 | 99 |
| Comparative Example 2 | #11-2 | Rice bran pickles | Gram positive Cocci | *Pediococcus ethanolidurans* Z-9 NR_043291.1 | 98 |
| Comparative Example 3 | A | Kimchi | Gram positive Cocci | *Leuconostoc citreum* KM20 NR_074694.1 | 100 |

TABLE 2

| No. | Strain | Gram stain | Activity (U/mg) |
|---|---|---|---|
| Example 1 | #11-1 | Gram-positive Bacilli | 165 ± 35 (n = 2) |
| Comparative Example 1 | #4 | Gram-positive Bacilli | 6.7 |
| Comparative Example 2 | #11-2 | Gram-positive Cocci | 2.7 |
| Comparative Example 3 | A | Gram-positive Cocci | 43 |

As the result of measurements of an activity for activating innate immunity of lactic acid bacteria of the present invention, as shown in Table 2, the activity of *L. paraplantarum* #11-1 of Example 1 was 165 U/mg and #11-1 had a significantly high activity for activating innate immunity.

Further, as shown in Table 2, with comparison of measurement results of "an activity for activating innate immunity (U/mg)" of Example 1 and Comparative Examples 1 and 2, *L. paraplantarum* #11-1 of the present invention showed an much higher activity for activating innate immunity, compared with other strains obtained from rice bran pickles.

In addition, an activity for activating innate immunity of *Leuconostoc citreum* KM20, known as "vegetable lactic acid bacteria" was 43 U/mg and lower than that of *L. paraplantarum* #11-1 of the present invention (Comparative Example 3).

Comparative Example 4

With the exception of using *Lactobacillus bulgaricus* OLL1073 strain instead of the *L. paraplantarum* #11-1 strain in Example 1, an activity for activating innate immunity was measured in the same matter as Example 1.

Comparative Example 5

With the exception of using *Lactobacillus casei* YIT9029 strain instead of the *L. paraplantarum* #11-1 strain in Example 1, an activity for activating innate immunity was measured in the same matter as Example 1.

Comparative Example 6

With the exception of using *Lactococcus lactis* JCM5805 strain instead of the *L. paraplantarum* #11-1 strain in Example 1, an activity for activating innate immunity was measured in the same matter as Example 1.

The results of Comparative Examples 4 to 6 are shown in Table 3.

TABLE 3

| No. | Strain | Activity (U/mg) |
|---|---|---|
| Comparative Example 4 | *Lactobacillus bulgaricus* | 24 |
| Comparative Example 5 | *Lactobacillus casei* | 5.6 |
| Comparative Example 6 | *Lactococcus lactis* | 17 |

Lactic acid bacteria of Comparative Examples 4 to 6 are lactic acid bacteria which are actually used in the manufacture of commercial fermented milk.

As shown in Table 3, lactic acid bacteria #11-1 of the present invention of Example 1 had a higher activity for activating innate immunity, compared with lactic acid bacteria of Comparative Examples 4 to 6.

When the sterilized material of *Lactobacillus paraplantarum* #11-1 of the present invention was measured, the activity for activating innate immunity was significantly high, and it was found that lactic acid bacteria of the present invention, dead bacteria of the lactic acid bacteria of the present invention, or processed material of the lactic acid bacteria of the present (for example, cultured material, concentrated material, paste material, dried material such as spray-dried material, freeze-dried material, vacuum-dried material and drum-dried material, fluid material, diluted material, crushed material, sterilized material of the lactic acid bacteria, and extract from the cultured material) were highly suitable as an innate immunity activator.

In addition, it has been already known that *Lactobacillus paraplantarum* has safety as fermented food.

Food and drink obtained by fermenting milk using *L. paraplantarum* #11-1 of the present invention has an activity for activating innate immunity.

Example 2

<Test for Effect Against Bacterial Infection>

"*Lactobacillus plantarum* subsp. *plantarum* JCM 1057" (hereinafter abbreviated as "*L. plantarum* PGN", also in FIG. 3) belonging to *Lactobacillus plantarum*, obtained from RIKEN, peptidoglycan fraction was prepared in accordance with an ordinary method, 2.7 mass % of the peptidoglycan fraction was mixed with an artificial diet of silkworms, and the mixed diet was given to silkworms for 2 days. That is, 0.041 g in total was given before injection.

Then, as described below, the effect of peptidoglycan of *Lactobacillus plantarum* on *P. aeruginosa* infection was investigated.

*Pseudomonas aeruginosa* (PAO1) was cultured at 30° C. for overnight. The bacteria liquid was diluted with saline to 1000-fold, and 50 μL of the dilution was injected into body liquid of silkworm.

After injection, feeding peptidoglycan to silkworm was stopped, the silkworm was grown at 27° C., and the survival of silkworms was counted with time.

Figure 3:
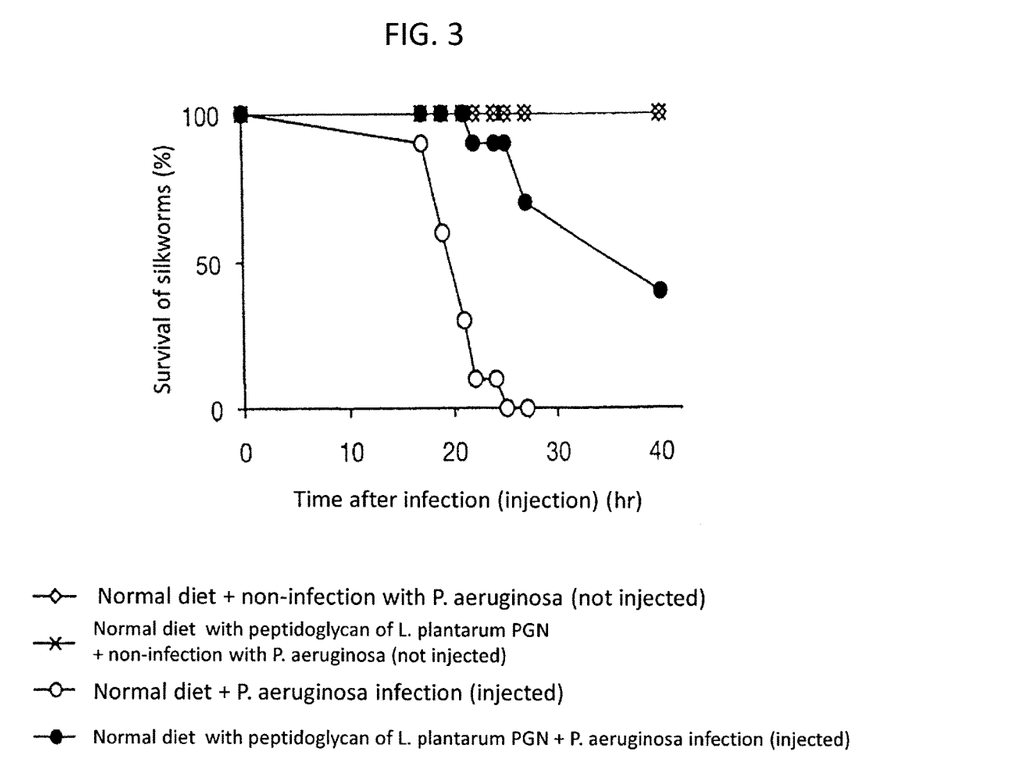
FIG. 3 is a graph showing survival time after *P. aeruginosa* infection of silkworm eating peptidoglycan fraction of *Lactobacillus plantarum* PGN and silkworm not eating the faction.

As shown in FIG. 3, silkworms eating the peptidoglycan fraction of *Lactobacillus plantarum* had longer survival time after *P. aeruginosa* infection compared with silkworms not eating the peptidoglycan fraction of *Lactobacillus plantarum*.

With the peptidoglycan fraction of *Lactobacillus plantarum*, tolerance to *P. aeruginosa* infection was given to the silkworms.

It was thought that the orally administered peptidoglycan of *Lactobacillus plantarum* activated a mechanism of innate immunity of intestine of the silkworm, and exhibited effect on infection control.

It was found that an agent comprising peptidoglycan of *Lactobacillus plantarum* as an active ingredient was useful as an agent for preventing or treating infection for mammals such as humans.

Further, it has been known that food fermented with *Lactobacillus plantarum* has safety. Thus, the agent for preventing or treating infection comprising peptidoglycan of *Lactobacillus plantarum* as an active ingredient is useful as food and drink for mammals such as humans.

Example 3

<Manufacture of Innate Immunity Activator and Agent for Preventing or Treating Infection>
<<Tablet>>

The culture medium of #11-1 is subjected to sterilization at 121° C. for 20 minutes. After 20.0 mg of the concentrated culture medium of #11-1, 40 mg of lactose, 20 mg of starch, and 5 mg of low-degree substituted hydroxypropyl cellulose were uniformly mixed, granules for tablets were prepared by a wet granulation method by using 8 mass % of aqueous solution of hydroxypropyl cellulose as a binding material. To this was added 0.5 to 1 mg of magnesium stearate, amount necessary to afford sliding properties to the granules, and then they were tableted by a tableting machine.

<<Solution>>

Inject solution was prepared by dissolving 10.0 mg of the above concentrated culture medium of #11-1, 2 mass % of aqueous solution of 2-hydroxypropyl-β-cyclodestrin.

INDUSTRIAL APPLICABILITY

The novel lactic acid bacterium of the present invention or processed material thereof has a high activity for activating innate immunity and effect for preventing or treating infection. Thus, a medicine or food and drink comprising an innate immunity activator activating innate immunity or an agent for preventing or treating infection which utilizes the lactic acid bacterium of the present invention, can be provided, and they are widely available in pharmaceutical industry, food industry, etc.

The present application is based on the Japanese Patent Application No. 2015-022567 filed on Feb. 6, 2015; and entire contents of the application are cited and incorporated herein as the disclosure of the specifications of the present invention.

[Accession No.]

NITE BP-02005

[Sequence Chart Free Text]

SEQ ID NO: 1 of the Sequencing Listing shows the nucleotide sequence of almost entire length of 16S rRNA of unknown strain belonging to genus *Lactobacillus*.

The invention claimed is:

1. An innate immunity activator comprising a processed material of a lactic acid bacterium belonging to genus *Lactobacillus* with Accession No. NITE BP-02005 in NITE Patent Microorganisms Depositary (NPMD) of Incorporated Administrative Agency National Institute of Technology and Evaluation (NITE),
wherein the processed material of the lactic acid bacterium is at least one of the processed materials selected from the group consisting of concentrated material, paste material, dried material, crushed material, and sterilized material of the lactic acid bacteria.

2. The innate immunity activator according to claim 1, wherein the processed material is dried material, and the dried material is spray-dried material, freeze-dried material, vacuum-dried material, or drum-dried material.

3. The innate immunity activator according to claim 1, wherein the processed material is sterilized material, and the sterilized material is material sterilized by heat, irradiation or crushing.

4. Food and drink comprising the innate immunity activator according to claim 1,
wherein the food and drink is a sweet snack, a taste beverage, a dairy product, a processed vegetable or fruit product, liquid food, a processed grain product, or a seasoning.

5. A medicine comprising the innate immunity activator according to claim 1,
wherein the medicine is an oral solid agent.

6. A method for activating innate immunity comprising a step of administering to a subject in need thereof a lactic acid bacterium belonging to genus *Lactobacillus* with Accession No. NITE BP-02005 in NITE Patent Microorganisms Depositary (NPMD) of Incorporated Administrative Agency National Institute of Technology and Evaluation (NITE), a dead bacterium of the lactic acid bacterium, or a processed material of the lactic acid bacterium as an active ingredient,
wherein the processed material of the lactic acid bacterium is at least one of the processed materials selected from the group consisting of cultured material, concentrated material, paste material, dried material, fluid material, diluted material, crushed material, sterilized material of the lactic acid bacteria, and extract from the culture material.

7. A method for preventing or treating infection comprising a step of administering to a subject in need thereof a lactic acid bacterium belonging to genus *Lactobacillus* with Accession No. NITE BP-02005 in NITE Patent Microorganisms Depositary (NPMD) of Incorporated Administrative Agency National Institute of Technology and Evaluation (NITE), a killed bacterium of the lactic acid bacterium, or a treated bacterium of the lactic acid bacterium as an active ingredient,
wherein the processed material of the lactic acid bacterium is at least one of the processed materials selected from the group consisting of cultured material, concentrated material, paste material, dried material, fluid material, diluted material, crushed material, sterilized material of the lactic acid bacteria, and extract from the culture material.

8. The method for preventing or treating infection according to claim 7, wherein the infection is caused by *Pseudomonas aeruginosa*.

* * * * *

SEQUENCE LISTING

```
<160> NUMBER OF SEQ ID NOS: 1

<210> SEQ ID NO 1
<211> LENGTH: 1480
<212> TYPE: DNA
<213> ORGANISM: Lactobacillus paraplantarum
<220> FEATURE:
<221> NAME/KEY: misc_feature
<222> LOCATION: (4)..(6)
<223> OTHER INFORMATION: n is a, c, g, or t
<220> FEATURE:
<221> NAME/KEY: misc_feature
<222> LOCATION: (1473)..(1473)
<223> OTHER INFORMATION: n is a, c, g, or t

<400> SEQUENCE: 1
ctannntgca agtcgaacga actctggtta atgattgaag gtgcttgcac ctgattgatt    60
taacatttga gtgagtggcg aactggtgag taacacgtgg gaaacctgcc cagaagtggg   120
ggataacacc tggaaacaga tgctaatacc gcataacaac tcggaccgca tggtctgagt   180
ttaaaagatg gcttcggcta tcacttttgg atggtccgc ggcgtattag ctagatggtg    240
aggtaacggc tcaccatggc aatgatacgt agccgacctg agagggtaat cggccacatt   300
gggactgaga cacggcccaa actcctacgg gaggcagcag tagggaatct tccacaatgg   360
```

-continued

```
acgaaagtct gatggagcaa cgccgcgtga gtgaagaagg gtttcggctc gtaaaactct    420
gttgttaaag aagaacatat ctgagagtaa ctgttcaggt attgacggta tttaaccaga    480
aagccacggc taactacgtg ccagcagccg cggtaatacg taggtggcaa gcgttatccg    540
gatttattgg gcgtaaagcg agcgcaggcg gttttttaag tctgatgtga aagccttcgg    600
ctcaaccgaa gaagtgcatc ggaaactggg aaacttgagt gcagaaaagg acagtggaac    660
tccatgtgta gcggtgaaat gcgtagatat atggaagaac accagtggcg aaggcggctg    720
tctggtctgt aactgacgct gaggctcgaa agtatgggta gcaaacagga ttagataccc    780
tggtagtcca taccgtaaac gatgaatgct aagtgttgga gggtttccgc ccttcagtgc    840
tgcagctaac gcattaagca ttccgcctgg ggagtacggc cgcaaggctg aaactcaaag    900
gaattgacgg gggcccgcac aagcggtgga gcatgtggtt taattcgaag ctacgcgaag    960
aaccttacca ggtcttgaca tactatgcaa atctaagaga ttagacgttc ccttcgggga   1020
catggataca ggtggtgcat ggttgtcgtc agctcgtgtc gtgagatgtt gggttaagtc   1080
ccgcaacgag cgcaacccct attattagtt gccagcatta agttgggcac tctagtgaga   1140
ctgccggtga caaaccggag gaaggtgggg atgacgtcaa atcatcatgc cccttatgac   1200
ctgggctaca cacgtgctac aatggatggt acaacgagtt gcgaactcgc gagagtaagc   1260
taatctctta aagccattct cagttcggat tgtaggctgc aactcgccta catgaagtcg   1320
gaatcgctag taatcgcgga tcagcatgcc gcggtgaata cgttcccggg ccttgtacac   1380
accgcccgtc acaccatgag agtttgtaac acccaaagtc ggtggggtaa ccttcgggga   1440
ccagccgcct aaggtgggac agatgattag ggngaagtcg                         1480
```